United States Patent [19]

Gravina et al.

[11] Patent Number: 4,517,161
[45] Date of Patent: May 14, 1985

[54] COMBUSTIBLE VAPOR DETECTION SYSTEM

[75] Inventors: Anthony N. Gravina, Deer Park; Murray Keitel, Kings Park; Harvey Weiss, Port Jefferson; Joseph N. Wiley, Dix Hills; Edmund G. Charland, Jr., Selden, all of N.Y.

[73] Assignee: Grumman Aerospace Corp., Bethpage, N.Y.

[21] Appl. No.: 426,608

[22] Filed: Sep. 29, 1982

[51] Int. Cl.$^3$ .................... G01N 27/16; G08B 21/00
[52] U.S. Cl. ........................................ 422/95; 422/94; 73/27 R; 340/634; 324/71.5
[58] Field of Search ............ 422/95, 98, 88, 90, 422/94, 96, 97; 340/634; 324/71.5; 73/23, 27 R

[56] References Cited

U.S. PATENT DOCUMENTS

| | | | |
|---|---|---|---|
| 4,045,794 | 8/1977 | Ohta | 340/691 X |
| 4,088,986 | 5/1978 | Boucher | 340/237 |
| 4,285,473 | 8/1981 | Williams | 241/37.5 |

OTHER PUBLICATIONS

Manual for Figaro Gas Sensor TGS #813, by Figaro Engineering Inc., Jul. 1, 1978.
Amendment of Solicitation/Modification of Contract Contractor: Grumman Aerospace Corporation Amendment to Statement of Work.

Primary Examiner—Barry S. Richman
Assistant Examiner—Joseph P. Carrier
Attorney, Agent, or Firm—Scully, Scott, Murphy & Presser

[57] ABSTRACT

A system for sensing and annunciating the presence at any one of a plurality of locations of accumulations of potentially hazardous gaseous and vapor mixtures prior to their reaching a lower explosive limit thereof. The system has particular applicability to aircraft, and has a number of advantageous features such as adjustable annunciator set points which are settable between relatively wide lower explosive level limits, compensation in the sensor circuitry for temperature variations, built in diagnostic and test features, and a circuit design wherein multiple sensors at multiple locations are operable independently of each other.

10 Claims, 6 Drawing Figures

COMBUSTIBLE VAPOR DETECTION SYSTEM

BACKGROUND OF THE INVENTION

1. Field of the Invention

The present invention relates generally to a gas detecting system for detecting and annunciating the presence and location of select gases at a plurality of locations, and more particularly pertains to a system for detecting and annunciating the presence and locations of accumulations of combustible vapor and air mixtures prior to their reaching a predefined hazardous level. The subject invention was designed in the context of a combustible vapor detection system for an aircraft, although the teachings herein are of a much broader nature. For instance, embodiments of the present invention might have direct suitability for detecting a combustible mixture of gas in a landfill or a mining environment wherein methane accumulations occasionally are known to present hazardous conditions. Also, many of the teachings herein, particularly those on the diagnostic features of the present invention, have direct application in gas detecting systems other than those designed particularly for the detection of combustible vapors.

2. Description of the Prior Art

Betz U.S. Pat. No. 3,997,837 discloses a gas analyzer system for monitoring the gaseous products of a process such as the exhaust gases from the combustion process of an oil burner. In Betz the electrical output of a semiconductor measuring cell is coupled to the noninverting or positive input of a differential amplifier, while the negative input thereof is coupled to a preset threshold voltage. When the positive output from the measuring cell exceeds the threshold voltage, the amplifier actuates several relays which control, for example, regulation and alarm devices, and an indicating element such as an LED annunciator. However, Betz is designed for a different type of application than the present invention, and suggests, for example, that a plurality of measuring locations can be monitored by automatically and sequentially connecting a plurality of measuring sensors to one differential amplifier. This reference also suggests that it is often appropriate to combine the signals from a plurality of measuring sensors to form a common output signal. The processing of a plurality of the sensor output signals in a manner as suggested by Betz would be clearly inappropriate to the type of combustible vapor detection system of the present invention.

Gas sensing elements constructed from a semiconductive material such as tin oxide which changes its resistance/conductance in dependence upon its surface adsorption of select types of gases have been developed by the Figaro Engineering Corporation of Osaka, Japan, and are disclosed in different stages of development in Taguchi U.S. Pat. No. 3,625,756, Taguchi U.S. Pat. No. 3,695,848, and Taguchi U.S. Pat. No. 3,900,815. These types of gas sensors are quite well known in the prior art as TGS (Taguchi Gas Sensor) sensors. TGS sensors are generally heated by an associated heating element, and are the type of sensor utilized in one designed and operable embodiment of the present invention. The types of sensors offered by the prior art, however, were not originally designed for an aerospace application as concerns the present invention. However, TGS sensors can be adapted to different applications by selectively doping them to improve their sensitivity to given types of gases.

Klass U.S. Pat. No. 3,864,628 is also somewhat pertinent to the present invention by disclosing TGS sensors utilized in combination with selective gaseous permeable membranes. This reference also discusses alarm techniques and annunciation set levels which can be utilized with a TGS sensor.

SUMMARY OF THE INVENTION

Accordingly, a primary object of the present invention is the provision of a system for sensing and annunciating in a timely manner the presence and location of accumulations of select gases at a plurality of locations.

A more specific object of the present invention to provide a system for sensing and annunciating the presence and locations of accumulations of potentially hazardous gaseous and vapor mixtures prior to their reaching a 100 percent lower explosive limit thereof.

A further object of the subject invention is the provision of a combustible vapor detection system as described having particular applicability to aircraft, and having a number of advantageous features such as adjustable annunciator set points which are settable between relatively wide lower explosive level limits, compensation for temperature variations, built in diagnostic and test features, and a system wherein multiple sensors at multiple locations in an aircraft are operable independently of each other to provide greater coverage and an ability to cover malfunctioning sensors.

In accordance with the teachings herein, the present invention provides a system for detecting and annunciating in a timely manner the presence and location of select gases at any one of several locations. A plurality of gas detectors are provided, one for each location being monitored. Each gas detector has a variable resistance characteristic such that its resistance varies in dependence upon the concentration of the select gas, and it produces an electrical output signal which varies in dependence thereon. A central control system is coupled to receive the electrical output signals, and compares each signal with a threshold unique to that sensor channel. An over-all annunciation signal is generated when any one of the output signals surpasses its particular threshold, and an annunciator indicator is provided for each detector to annunciate the presence of the detected gas at that location to the operator. An important feature of the subject invention is the provision of diagnostic circuits for testing the operation of the gas detection system at any time and indicating any malfunctions thereof to the operator.

The present invention was particularly designed for the detection of combustible hydrocarbon vapors in an aircraft wherein each detector is placed at a location on board thereof at which hydrocarbon vapors may be present. For instance, a combustible vapor detector might typically be placed in the electronics bay of an aircraft through which fuel lines run. In the event of detected hydrocarbon fuel vapors, the electronic equipment in the bay, which might include high power radar equipment, could be turned off, either manually by the pilot or automatically. In this particular application, the threshold for each vapor detector is set at a level corresponding to a fraction of the concentration of hydrocarbon vapors in air which will just support combustion, known as the lower explosive limit. However, different levels of other gas species could be similarly detected by judicious selection of the threshold level. With such capability the present invention may be adaptable to sense multiple vapors at different locations.

Another particularly advantageous feature of the present invention allows for the separate setting of the threshold signal for each gas detector, such that the individual characteristics of each gas detector is considered in setting its threshold.

The electronics of the present invention also provides a number of very advantageous design features, including a redundant type of design wherein a separate electrical channel is provided for each gas detector. Each electrical channel includes separate power supplies and separate signal processing circuitry. In greater detail, each separate electrical channel is constructed as a dedicated printed circuit board for that channel, such that a plurality of substantially identical PC boards are provided, one for each detector channel. Moreover, pursuant to diagnostic features of the present invention, each circuit board includes at least one annunciator light thereon for indicating proper operation of the electronic components in that channel from the viewpoint of system continuity.

In accordance with the teachings of the preferred embodiment, each gas detector comprises a semiconductor type of gas detecting element known as a TGS detector wherein adsorption of a select type of gas on its surface decreases its resistance. A heater element is provided for each semiconductor element for thermal activation of the surface reactions thereon. Moreover each detector has a temperature compensation circuit, including a thermistor, for providing thermally stable operation of the gas detector. Each circuit board includes first and second power supplies, the first for the gas detecting element and the second for the heater element. Pursuant to the diagnostic features of the preferred embodiment, five annunciator LEDs are provided on each circuit board, with the first and second LEDs signaling proper operation of the first and second power supplies, the third LED indicating continuity of the semiconductor gas detecting element, the fourth LED indicating proper operation of the temperature compensation circuit, and the fifth LED indicating continuity of the heater element associated with the gas detecting element. The diagnostic features of the preferred embodiment enable all annunciator LED indicators during an operational test in which all of the tested components are functional.

Inventive mechanical features of the present invention include a unique housing for each combustible vapor detector and also a unique mounting for each detector.

The housing for each combustible vapor detector is designed to provide explosion suppression and flame arresting functions through the use of dual 100 mesh screens. The housing defines an input port for the detector, over which first and second spaced fine mesh screens are positioned. The spaced fine mesh screens virtually ensure provision of effective explosion suppression and flame arresting functions. In the preferred embodiment herein, the first and second fine mesh screens define respectively smaller and larger convex shaped surfaces which are positioned over the input port of the housing and the detector element therein.

A unique mounting for each vapor detector is designed for operation in an environment subject to vibration, such as on board an aircraft. The unique mounting includes a plurality of resilient vibration attenuators which are positioned between a mounting bracket and the detecting element to provide vibration and shock isolation and attenuation therefor. The detecting element is secured to the mounting bracket by a plurality of screws, and an attenuator is mounted on each screw shaft between the bracket and the detecting element. The screws are selectively tightenable to tune the vibration attenuation to minimize the transmission to the detecting element of vibrational frequencies which are particularly detrimental to its operation. In the preferred embodiment, each resilient vibration attenuator is in the form of a rubber grommet.

BRIEF DESCRIPTION OF THE DRAWINGS

The foregoing objects and advantages of the present invention for a combustible vapor detection system may be more readily understood by one skilled in the art, with reference being had to the following detailed description of a preferred embodiment thereof, taken in conjunction with the accompanying drawings wherein like elements are designated by identical reference numerals throughout the several views; and in which.

DETAILED DESCRIPTION OF THE DRAWINGS

Figure 1:
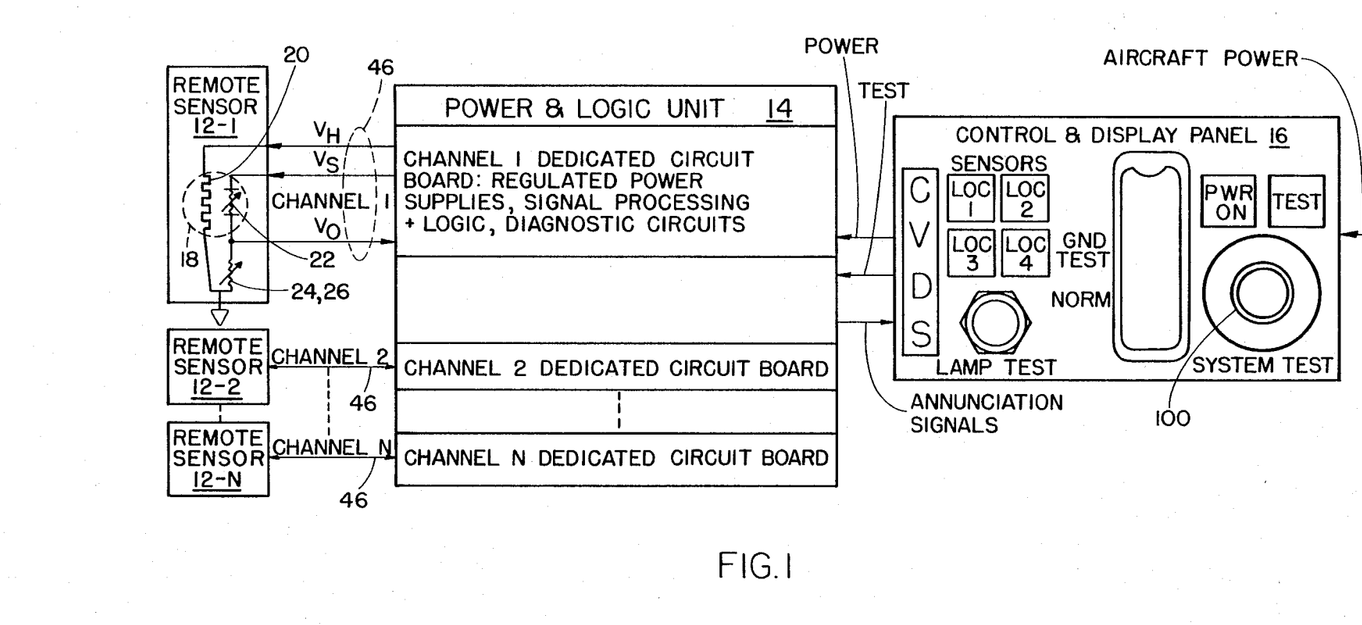
FIG. 1 is a block diagram of the major components of an exemplary embodiment of a combustible vapor detection system constructed pursuant to the teachings of the present invention.

Referring in detail to the drawings, FIG. 1 illustrates a block diagram of the major components of a Combustible Vapor Detection System (CVDS) designed to reliably detect and annunciate in a timely manner the presence and location of a potentially hazardous accumulation of vapor and air mixtures prior to its reaching a 100 percent lower explosive limit (LEL). The system includes a plurality of channels 1 through N for a plurality of remote sensors 12-L through 12-N positioned at each of N locations on an aircraft, at each of which a hazardous accumulation of combustible or explosive air vapor might be present, a single power and logic circuit 14, and a single control and display panel 16.

A typical embodiment of the present invention may use four sensors positioned at four locations of concern on an aircraft, represented by four annunciator warning lights labeled LOC1, LOC2, LOC3 and LOC4 on the display panel 16. The display panel for the combustible vapor detection system also includes power "on" and test indicator lamps for the system, a lamp test switch designed to functionally validate the operation and integrity of the four alarm lamps and the power "on" and test lamps, and a system test switch to activate a diagnostic testing procedure, as described in greater detail hereinbelow.

Operationally, a remote sensor 12 detects the presence of a contaminant gas representing a hazard at the sensor location, and is responsive thereto so as to generate an analog output signal for the power and logic circuit 14. The power and logic circuit 14 determines if the output signal of the remote sensor 12 exceeds a predetermined threshold level and, responsive thereto, causes an annunciation to be displayed on the control and display panel 16, which alerts the pilot as to the presence and location of each potential hazard.

Figure 2:
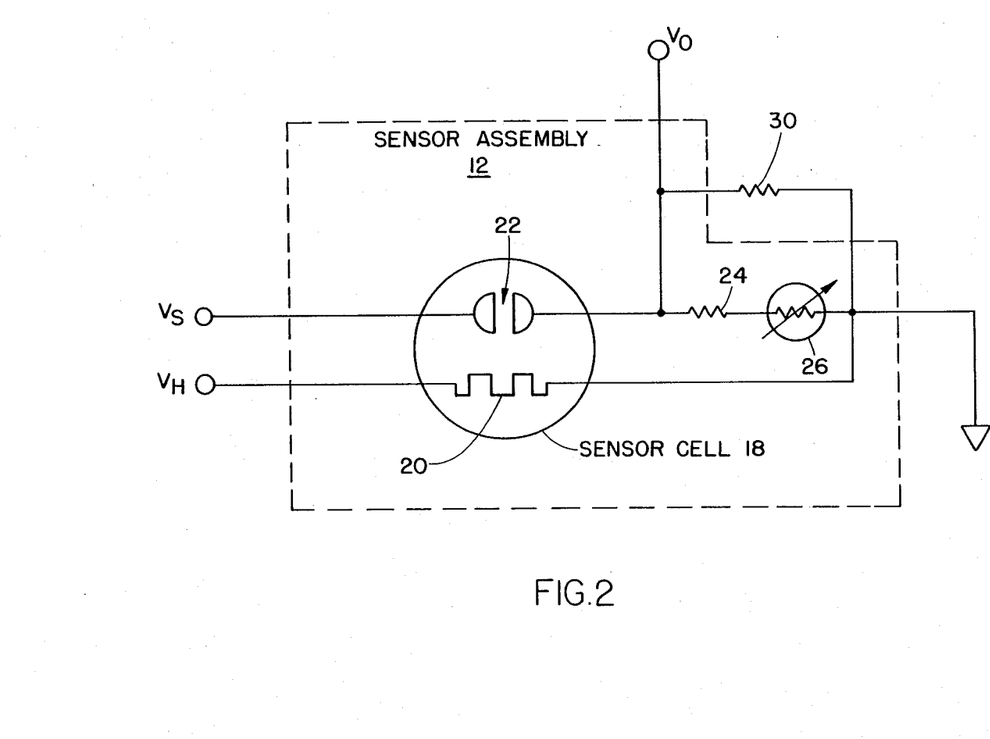
FIG. 2 illustrates the electrical components of the measurement circuit of each remote sensor assembly employed in the combustible vapor detection system.

Each remote sensor 12, as illustrated in FIGS. 1 and 2, comprises a sensor cell 18 having a heating element 20 and a sensor element 22. The sensor element 22 has the characteristics of a variable resistance, the value of which is determined by the concentration of contaminating gases through surface absorption-desorption phenomena, such that the resistance of the sensor element decreases with an increase in the concentration of the contaminating gas being detected. Each remote sensor 12 is calibrated to provide an output voltage $V_O$ which is a function of the concentration of a specific gas mixture in air, expressed herein as a percentage of a Lower Explosive Level (% LEL), where 100% LEL represents that concentration of the specific gas in air which will just support combustion. A voltage is selected for each sensor 12 which represents a predetermined safe % LEL, as determined by the sensor calibration, and is set as the annunciation or threshold level for that particular channel. Each channel of the system is set to annunciate at a given % LEL, and if the output signal of that sensor exceeds its threshold, annunciation occurs for that channel.

The sensor cell 18 is coupled in series with a fixed load resistor 24 and a temperature compensating element in the form of a temperature responsive resistor (thermistor) 26. During operation, a fixed voltage $V_S$(15 VDC) is applied across the series connected resistances 22, 24, 26, which then function as a voltage divider, with the output voltage $V_O$ between elements 22 and 24 varying in the presence of a contaminant gas.

Each sensor element 22 may comprise a commercially available bulk semiconductor, such as tin oxide ($SnO_2$), the resistance of which varies as described above. These types of sensor elements are known commercially as TGS sensors, for Taguchi Gas Sensor. The construction of the sensor element 22 allows adsorption of oxygen to form potential barriers at grain boundaries, which oppose free electron flow, thus resulting in a substantial increase in the resistance of the semiconductor material. When the surface of the sensor element is exposed to hydrocarbons or other chemically reducing environments, adsorption occurs at the surface with the resultant neutralization of the opposing potential barriers, thus reversing the previous reaction at the surface. The hydrocarbon presence results in increased density and mobility of conducting electrons in the semiconductor space charge region by decreasing the potential barriers at the grain boundaries. Accordingly, the hydrocarbon presence results in a substantial decrease in the resistance of the semiconductor, and this results in an increase of output voltage $V_O$ in the voltage divider network 22, 24. When the output voltage $V_O$ exceeds a threshold value indicative of the preset % LEL, the power and logic unit 14 causes an annunciation to occur on the display panel 16. One advantage of this type of detector element is that it will also detect and react to smoke in the aircraft, in addition to detecting hydrocarbons.

The heater 20 functions to preclude absorption by the sensor element 22 of unwanted contaminants in clean air, and also acts to thermally activate surface reactions with contaminants. In the illustrated embodiment, the heater 20 is supplied with electrical power by a separate power supply $V_H$ (5 VDC). The heater element improves the response time of the electro-molecular action by thermally stabilizing the reactive surface of the sensor element 22. The heater 20 can raise the temperature of the air surrounding the semiconductor cell 22 in the magnitude of 200° to 400° C.

Circuitry for temperature compensation within the range of from approximately 0° to 160° F. is provided by the series-coupled thermistor 26 and resistor 24, both connected in parallel with a resistor 30. The mistor 26 has the usual temperature-dependent characteristic of a thermistor in which its resistance varies inversely in proportion to temperature. The temperature varying response of the thermistor 26 in this temperature compensation circuit virtually assures thermal stability of the sensor 12 over an extremely broad temperature range.

The operation of each remote sensor 12 is completely independent of every other remote sensor 12 because dedicated circuitry in the power and logic unit 14 supplies each channel and remote sensor 12 with supply voltages $V_S$ and $V_H$ and also processes the output signal $V_O$ of each individual sensor 12. Accordingly, the failure of a component in any one channel would not affect the performance and proper operation of other channels of the system.

The power and logic unit 14 contains the power supplies to supply the voltages $V_S$ and $V_H$ to the individual sensors 12, and also includes circuitry to process the analog output voltage $V_O$ of each sensor. When an analog voltage $V_O$ exceeds a threshold value in terms of a safe % LEL, as explained herein above, an annunciation signal is generated. The power and logic unit also contains diagnostic Built In Test (BIT) sequences, as described in greater detail hereinbelow.

The control and display panel 16 provides the system interface with the pilot and enables the testing of the system, with various test functions as described below, and also functions as the annunciation display to alert the pilot to a potentially explosive level of combustible vapor in the aircraft.

Figure 3:
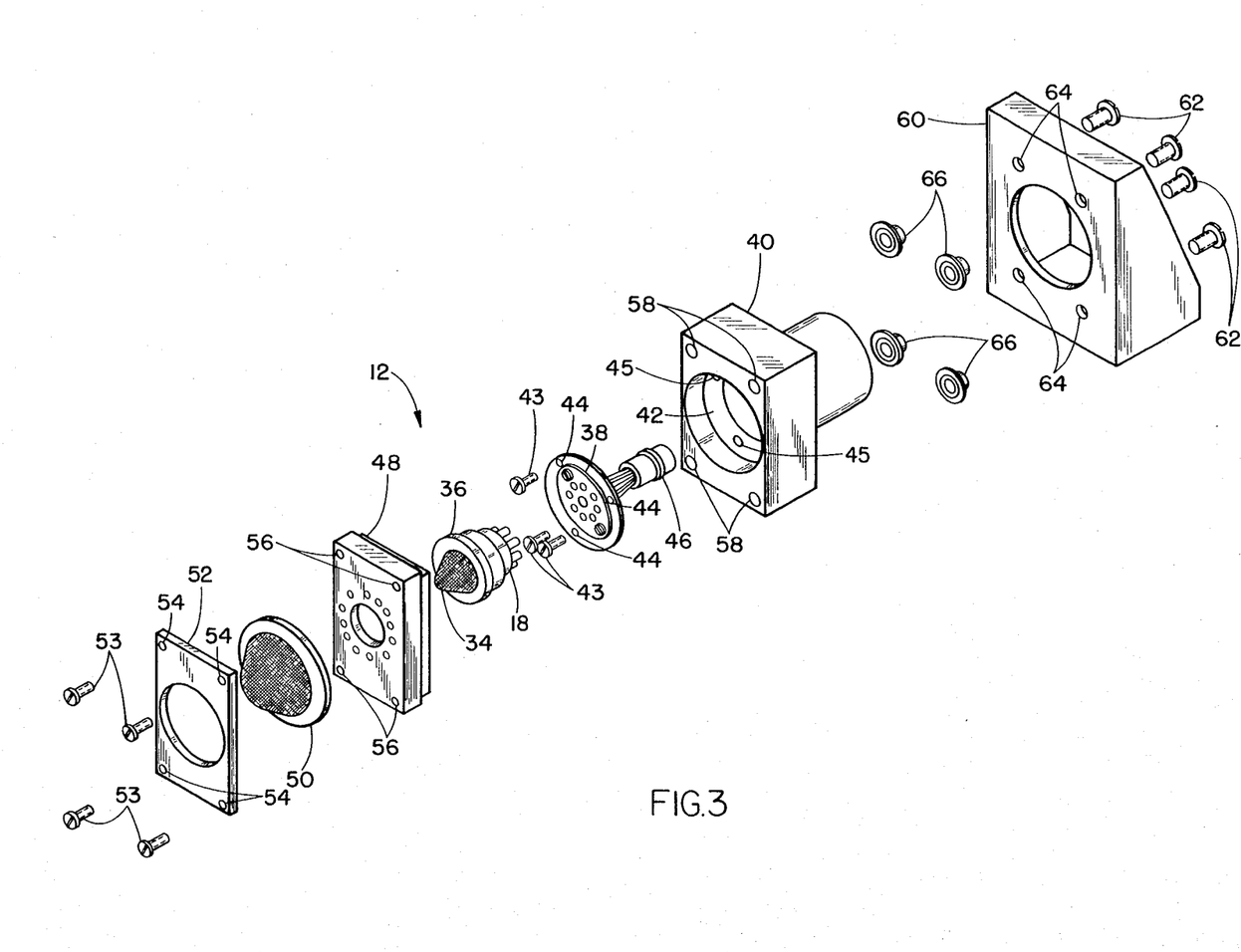
FIG. 3 illustrates an exploded view of the mechanical components of each remote sensor and its mounting bracket, and shows in particular the various mounting and vibration isolation components thereof.

FIG. 3 illustrates an exploded view of the components of one remote sensor unit 12. The sensor cell 18 is positioned behind a fine 100 mesh screen 34 which is secured in place by a retainer ring 36. The fine mesh screen 34 functions as both an input port and a flame arrestor for the sensor cell 18. A female electrical connector 38 couples to pin connectors projecting from the rear of the sensor cell 18, and supplies the several electrical connections shown in FIGS. 1 and 2. A housing 40 defines a circular recess or well 42 therein in which the electrical connector 38 is mounted by suitable fastener elements such as screws 43 extending through holes 44 in the periphery of the connector into suitable threaded apertures 45 formed in the housing 40. A shielded cable 46, only the forward section of which is shown in FIG. 3, extends from the remote sensor 12 through the aircraft to the power and logic unit 14.

A cover 48 is positioned over the sensor cell 18 on housing 40, and a second fine 100 mesh screen 50 is positioned over the cover 48 and is secured in place by a bezel 52. Suitable fasteners such as screws 53 extend through holes 54 in the bezel 52 and holes 56 in the cover 48 into suitably threaded apertures 58 in the housing 40. The second mesh screen 50 functions similar to the first mesh screen 34 to provide an input port and also flame arrestor structure for the sensor assembly 12. This structural combination of at least two spaced, strategically located fine mesh screens virtually ensures explosion suppression and flame arresting functions for the system in the event of arcing due to electrical malfunction within the cell 18.

The sensor assembly 12 is supported in position in the aircraft by a mounting bracket 60 to which it is secured by fasteners such as screws 62 extending through holes 64 in the bracket 60 into suitably positioned threaded apertures in the back of housing 40. Resilient vibration isolators or attenuators 66, which may be suitable rubber grommets, are provided around the shanks of screws 62 located between the bracket 60 housing 40, and provide a significant protective feature of the mounting structure for the remote sensor 12. The screws 62 and resilient isolators 66 provide vibration and shock attenuation for the sensor, and the screws 62, by selective tightening thereof, allow the vibration attenuation to be tuned to eliminate transmission to the sensor 12 of troublesome vibrational frequencies in the aircraft. Additionally, the attenuators or grommets may be suitably dimensioned in conformance with expected vibration frequencies and intensities. The manner in which the sensor is mounted in the mounting bracket is designed to attenuate frequencies which are detrimental to operation of the sensor cell, and will thus ensure dynamic stability of the system against encountered shocks and vibrations. The sensor assembly as described herein has been constructed and tested, and has proven to be rugged, dependable in operation and economical.

The sensor cell housing as described and illustrated herein is designed and configured to optimize the performance of the sensor. The sensor cell housing is also mounted to minimize water entrapment.

Figure 4:
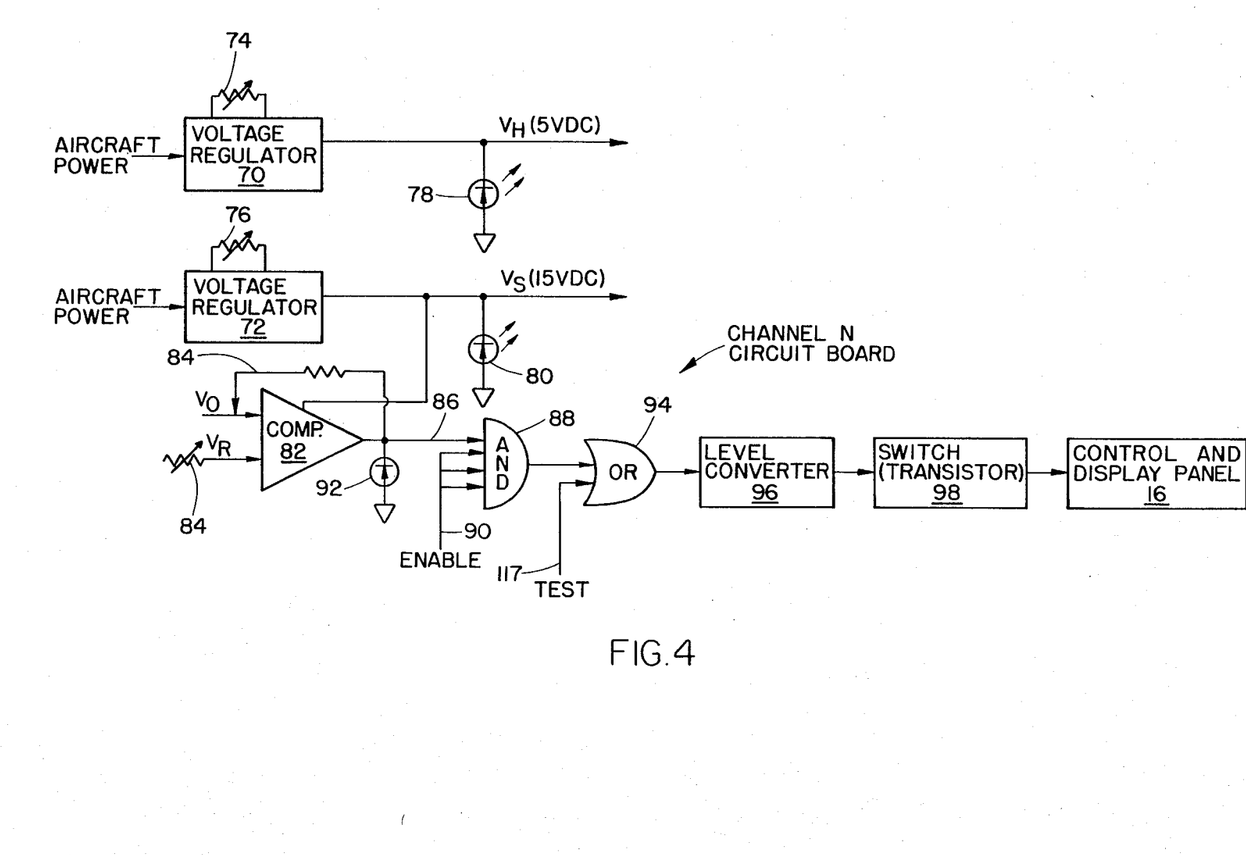
FIG. 4 is a block diagram of the major components of one channel of the power and logic circuit employed by the system.

FIG. 4 is a block diagram of the major components of one channel of the power and logic unit 14 (PLU). Power from the aircraft is supplied through the control and display 16 to the power and logic unit 14. The power and logic unit 14 includes separate dedicated circuitry for each channel, such that the failure of a component or circuit in one channel will not affect the operation of other channels.

The separate dedicated circuits for each channel includes two voltage regulator circuits 70 and 72 for supplying respectively the voltages $V_H$ (5 VDC) and $V_S$ (15 VDC), circuits for processing the output signal from the remote sensor for that channel, and diagnostic circuit connections. The separate dedicated circuits for each channel can be supplied on a separate dedicated printed circuit board, such that N channels would require N substantially identical circuit boards in the power and logic unit along with common connecting circuits therefor. Each voltage regulator circuit includes a trim potentiometer, respectively 74, 76, associated therewith in order to finely adjust its output supply voltage. Each voltage regulator circuit can also include a test point (not shown), as is commonly available on these circuits for testing thereof, and a light-emitting diode (LED), respectively 78, 80, to annunciate functionability of the voltage regulator circuit.

Each channel of the CVDS system is also provided with a voltage comparator 82, which may be of the quad type, wherein the output voltage $V_O$ provided by the sensor unit 12 for that channel is compared with a settable threshold voltage $V_R$, adjustable by a potentiometer 84 according to laboratory calibration data on the sensor unit 12 for that channel to a selected alarm annunciation threshold voltage.

Figure 5:
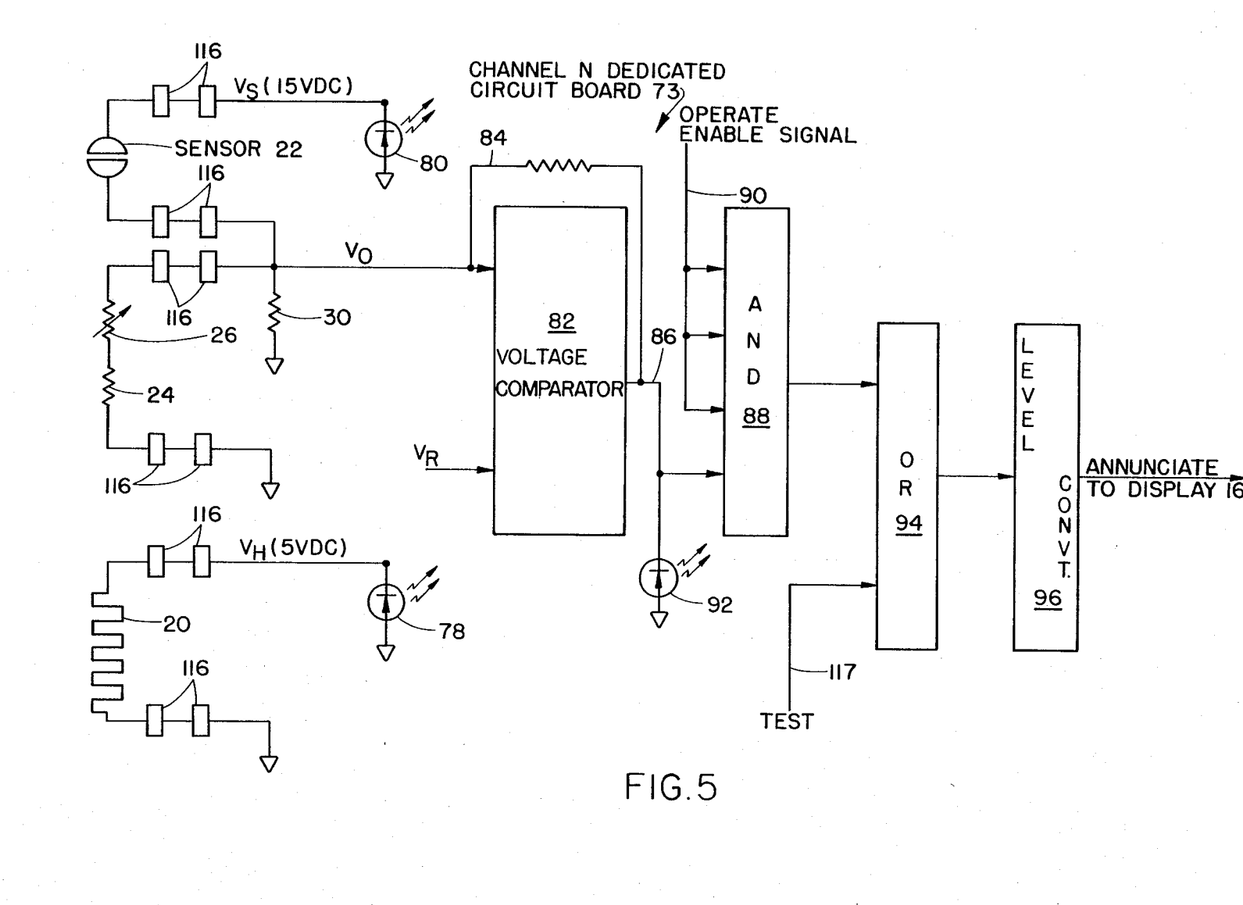
FIG. 5 is an electrical diagram illustrating further details of operation of one channel of the power and logic circuit.

FIGS. 4 and 5 illustrate normal operation of the CVDS system in the sensing mode. The voltage comparator 82 normally produces a low or zero voltage signal at its output when sensor voltage $V_O$ is less than the threshold voltage $V_R$ for that channel. However, if the sensor voltage $V_O$ reaches or exceeds the threshold voltage $V_R$, the comparator 82 produces a positive (+15 VDC) output signal. A small portion of this output signal is fed back on line 84 to the $V_O$ input line to assure a positive "snap action" switch-over when $V_O$ exceeds $V_R$.

When the sensor signal $V_O$ plus the positive feedback to the $V_O$ input of voltage comparator 82 is less than or equal to the reference voltage $V_R$ (as when changing from a positive to a more negative value) the comparator output is switched from +15 VDC back to 0 VDC, thereby interrupting the ground path for the alarm relay. Excellent "snap action" of the voltage comparator 82 is obtained because the positive feedback voltage is removed and the signal voltage becomes even more negative with respect to the reference voltage $V_R$. In one designed circuit, the threshold voltage for a positive going input was chosen to be 0.2 VDC more positive for annunication than turn-off for a negative going input. This "hysteresis" is added to preclude a hunt situation when the input signal $V_O$ approaches the set point or reference voltage $V_R$ from either direction.

The output signal of the comparator on line 86 is directed to an AND gate 88, which has as other inputs an enable signal on line 90 from the control panel 16 which is supplied thereto when the system is on. The reason for the plurality of inputs to AND gate 88 from line 90 will become apparent from the explanation of the diagnostic features of the present invention set forth hereinbelow. The output signal of the comparator on line 86 is also directed to an LED 92, normally on the printed circuit board, to annunciate proper operation of the circuit. The output signal of AND gate 80 is directed through an OR gate 94, the function of which is discussed below, the output of which is taken as an annunciate signal for that channel. Each channel can also include a level converter circuit 96, the output of which actuates a switch 98, such as a transistor, which completes a ground for an alarm relay in the control and display unit 16. Completion of the ground causes the relay to actuate, which causes the annunciation light LOC-N for that channel to illuminate, thereby indicating a potential hazard and identifying its location to the pilot of the aircraft.

The system also includes a Built-In-Test (BIT) diagnostic feature adapted to ensure the functionability of the system by enabling a pilot to individually test, at any time, the continuity of the sensor element, the temperature compensation circuitry, and the heater circuitry. The BIT feature will cause annunciation to occur on the system display panel 16 if each of the three aforementioned circuit portions is operational, and will preclude annunciation from occurring if any of the circuit portions has failed the tests in the BIT diagnostic feature.

Operation of a Built-In-Test (BIT) function incorporated within the power and logic unit 14 is divided into three functional areas, each corresponding to validation of the operation and performance of the heater, sensor, and temperature compensation network associated with each sensor assembly 12. Operation of the BIT function also tests a channel's corresponding power and logic circuitry in the power and logic unit 14 and the control-display panel 16. The BIT function can be actuated by depressing a test switch 100 on the control panel 16. An optional design could also provide an additional test switch in the power and logic unit to actuate the BIT function.

Figure 6:
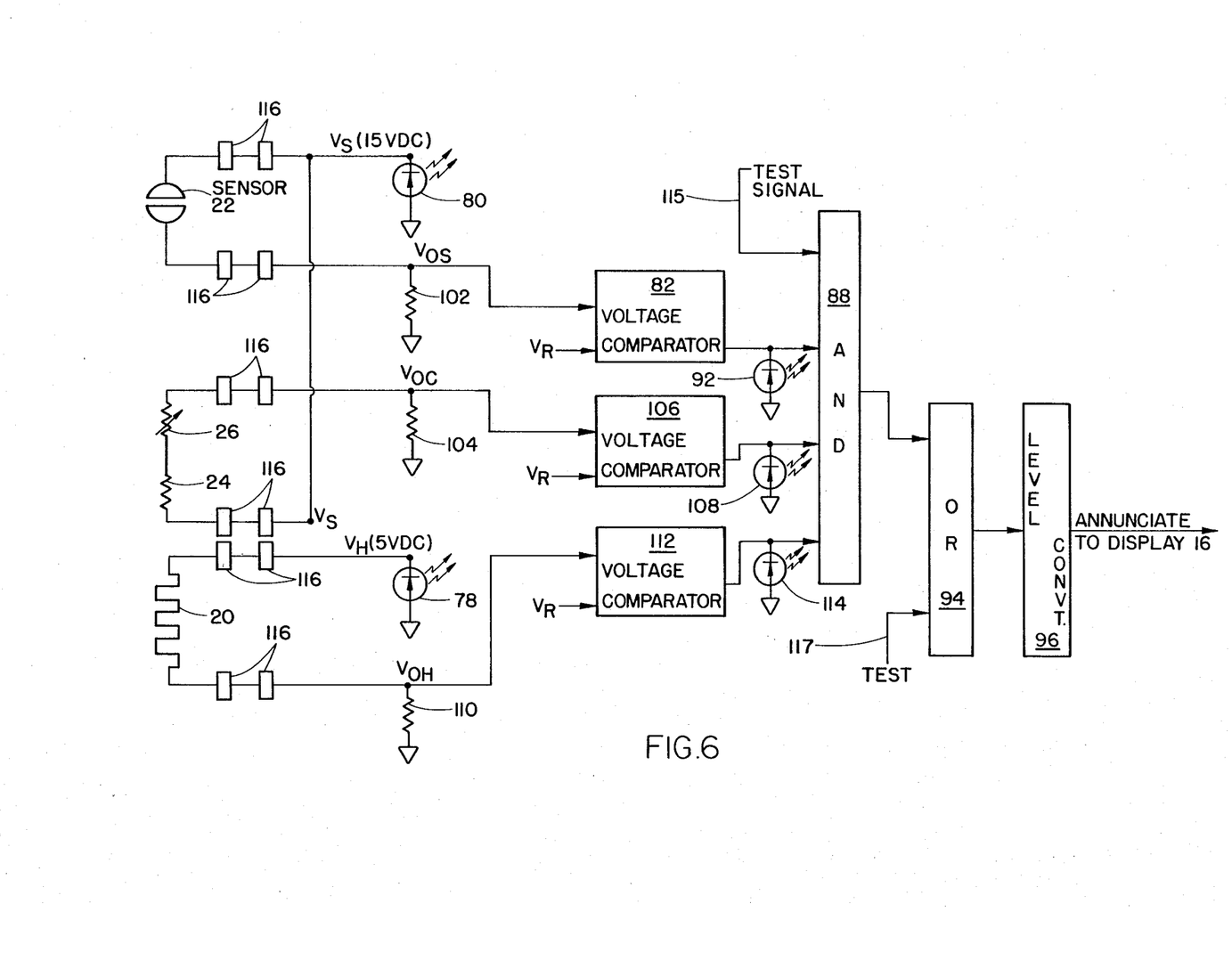
FIG. 6 is an electrical diagram similar to that of FIG. 5, illustrating the operation of several diagnostic features of the present invention.

The BIT function can be simply described by comparing the simplified block diagram of FIG. 5, which illustrates the normal operation of one sensor-PLU channel, with that of FIG. 6 which illustrates the same channel in the BIT mode. Basically, activation of the BIT function isolates the sensor element 22 from the compensator network 24, 26, and replaces the normal load resistor 24 with a test resistor 102 such that the resulting output voltage $V_{OS}$ from the isolated sensor 22 is greater than the reference voltage $V_R$. This results in the voltage comparator 82 going high and annunciation of diode 92 which completes the validation of the sensor circuit. The BIT function also isolates the temperature compensation network 24, 26, applies voltage $V_S$ thereto, and inserts another test resistor 104 into the circuit. The resultant output signal $V_{OC}$ is designed to be greater than the fixed reference voltage $V_R$. A voltage comparator 106, similar in concept and operation to voltage comparator 82, goes high, and an annunciator LED 108 is illuminated, completing the validation of the temperature compensation network. Finally, the BIT function isolates the heater element 20, applies voltage $V_H$ thereto, and inserts a third test resistor 110 in the circuit. The resultant output signal $V_{OH}$ is designed to be greater than the fixed reference voltage $V_R$. A voltage comparator 112, similar in concept and operation to voltage comparator 82, goes high, and an annunciator LED 114 is illuminated, completing validation of the heater circuit.

During the BIT diagnostic testing sequence, a test signal is supplied to AND gate 88 on line 115, and if all of the tested components are operating correctly, the other three inputs to the AND gate will also be high, thereby enabling the AND gate and illuminating the annunciator warning light for that channel. All of the other channels are simultaneously tested by the BIT diagnostic sequence in a similar manner, such that all of the annunciator warning lights in the display panel 16 will be illuminated if all of the tested components of the system are operating. During normal operation of the system, illustrated in FIGS. 4 and 5, an enable input signal on line 90 is directed to three inputs of AND gate 88, and thus only an additional high output signal on line 86 is required for annunciation to occur in any one channel. The OR gate 94 passes on any annunciation signal from AND gate 88, and additionally has a test input line 117 which allows only the annunciator light to be tested by depression of the LAMP TEST switch on display panel 16.

The isolation of the various components during utilization of the BIT diagnostic feature is illustrated in FIGS. 5 and 6 by connections 116, which can be suitable switching components.

The BIT function utilizes both the $V_H$ and the $V_S$ power supplies in each channel so as to ensure validation of circuit continuity, as well as comparator and logic circuit operational integrity, and all external wiring associated with signal, operational and heater voltages. The LED displays 78, 80, 92, 108, 114 are located on each circuit board servicing that particular PLU channel. During operation in the BIT mode, all of the annunciator LEDs on all of the circuit boards should be lighted, and a nonlighted LED would allow a malfunction to be rapidly located and diagnosed.

The BIT function simulates an alarm condition and, as such, will result in an alarm indication on all of the LOC warning lights on the control and display console as well as a deactivation of all logically interconnected equipment, as described below. The combustible vapor detector system basically detects the presence and location of a potentially hazardous accumulation of vapor and air mixture prior to its reaching a selectable percent of its lower explosive limit. In addition to the annunciation thereof, the system can also be designed to shut off all nonessential equipment in the location of the potential hazard, such as high power electronic and electrical equipment (e.g. radar equipment) in the hazard area. Circuits and equipment for this function could be included in the control and display portion 16. One designed embodiment of the control and display unit 16 had five relays associated therewith, one alarm relay for each channel as already described above, and a fifth for a deactivation control logic for the entire system, not described in detail herein. Moreover, the designed embodiment also included a ground-test/normal switch, as illustrated in FIG. 1, designed to offer the pilot various options regarding utilized power supplies, and that function is also not described in detail herein since it is not pertinent to an understanding of the present invention.

Operation of the overall system is essentially automatic once electrical power has been supplied thereto. An initial activation of the CVDS system will generally cause all four LOC lamps to annunciate for as long as five minutes, depending upon the amount of time the system had been unpowered. This condition is inherent in the design, and is caused by normal atmosphere contaminants building up on the unpowered sensor cells, causing high cell conductance. These contaminants burn off under normal clean air conditions in a matter of minutes. It is important, however, to refrain from activating any potential ignition source until such time as all of the annunciators extinguish.

One designed embodiment of the present invention was constructed with CMOS logic designed to MIL-SPEC standards. Performance was very satisfactory in several operational environments. The concepts of the present invention are flexible and adaptable to many, varied applications and environments.

While one detailed embodiment and several variations of the present invention for a combustible gas detection system are described in detail herein, it should be apparent that the disclosure and teachings of the present invention will suggest many alternative designs to those skilled in the art.

What is claimed is:

1. A combustible vapor detection system for an aircraft for detecting and annunciating the pressure and location of combustible vapors at a plurality of locations on the aircraft, comprising:
   a. a plurality of combustible vapor detectors, each adapted to be placed at a location to be monitored on an aircraft at which combustible vapors may be present, each combustible vapor detector having a resistance which varies in dependence upon the concentration of a combustible vapor to be detected, such that it produces an electrical output signal which varies in dependence upon the concentration of the combustible vapor, each vapor detector comprising a semiconductor gas detecting element wherein adsorption of select types of gases on its surface decreases its resistance, and having a greater element for thermally activating surface reactions on the semi-conductor element, and each vapor detector having a temperature compensation circuit, including a thermistor, for providing thermally stable operation for the vapor detector;

b. a central control means, which receives the plurality of electrical output signals, comprising: (1) means for comparing each electrical signal with a separate threshold value for each vapor detector, such that individual characteristics of each vapor detector are considered in setting its threshold value, and the threshold value for each vapor detector being set at a level corresponding to a fraction of the concentration of combustible vapors in air which will just support combustion; (2) means for generating an annunciation signal when at least one of the electrical output signals surpasses its threshold value; (3) and a plurality of annunciator indicators, one corresponding to each combustible vapor detector, for signaling the occurrence of each annunciation signal to an operator; and (4) a separate electrical channel for each vapor detector, each separate electrical channel comprising a dedicated circuit board for that channel, each electrical channel including separate first and second power supplies, the first power supply being for the vapor detecting element and the second power supply being for the heater element, and each electrical channel including a separate signal processing circuit for comparing the electrical signal from the vapor detector for that channel with a threshold value for that channel, each said dedicated circuit board comprising annunicator lights thereon for indicating proper operation of the components of that electrical channel, said annunciator lights including five LEDs, first and second LEDs for indicating operation of the first and second power supplies, a third LEd for indicating operation of the semi-conductor vapor detecting element, a fourth LED for indicating operation of the temperature compensation circuit, and a fifth LED for indicating operation of the heater element; and c. diagnostic means for testing the combustible vapor detectors for operation, and for indicating a malfunction thereof to the operator.

2. A system as claimed in claim 1, wherein said diagnostic means are designed to enable all five LEDs on each circuit board, and further enable each annunciator indicator during an operational test in which all of the tested components are operating.

3. A system as claimed in claim 1, said central control means including a control and display unit, and said annunciator indicators comprising annunciator lights on said control and display unit.

4. A system as claimed in claim 3, said diagnostic means including a diagnostic testing switch on said control and display unit for actuating testing of the system.

5. A system as claimed in claim 1, further comprising:
   a. a housing for each combustible vapor detector element, and defining an input port therefor;
   b. a first fine mesh screen provided over said input port; and
   c. a second fine mesh screen spaced from said first fine mesh screen and also extending over said input port, to virtually ensure provision of effective explosion suppression and flame arresting functions.

6. A combustible vapor detecting system as claimed in claim 5, said combustible vapor detecting element comprising a semiconductor gas detecting element wherein adsorption of combustible vapors on its surface decreases its resistance, and a heater element for thermally activating surface reactions on the semiconductor element, whereby the first and second spaced fine mesh screens provide isolation of the heater element to provide effective explosion suppression and flame arresting functions.

7. A combustible vapor detecting system as claimed in claim 6, said first and second fine mesh screens defining respectively smaller and larger convex surfaces which are positioned, spaced from each other, over said input port and said detector element.

8. A combustible vapor detecting system as claimed in claim 1, further comprising:
   a. a mounting bracket for said detecting element;
   b. a plurality of resilient vibration attenuators positioned between said bracket and said detecting element for providing vibration and shock isolation and attenuation for the detecting element.

9. A combustible vapor detecting system as claimed in claim 8, said detecting element being secured to said mounting bracket by a plurality of screws, and said plurality of attenuators being mounted on the screw shafts between said mounting bracket and said detecting element, said screws being selectively tightenable to tune the vibration attenuation by said resilient attenuators to minimize transmission to the detecting element of vibration frequencies which are particularly detrimental to its operation.

10. A combustible vapor detecting system as claimed in claim 9, each resilient vibration attenuator comprising a rubber grommet.

* * * * *